(12) United States Patent
Dixit et al.

(10) Patent No.: US 9,364,451 B1
(45) Date of Patent: *Jun. 14, 2016

(54) ALTERNATING SYMPATHOMIMETIC THERAPY FOR THE TREATMENT OF RESPIRATORY AILMENTS

(71) Applicant: Sovereign Pharmaceuticals, LLC, Fort Worth, TX (US)

(72) Inventors: Suresh Dixit, Fort Worth, TX (US); Juan Carlos Menendez, North Richland Hills, TX (US); Ralph Brown, Southlake, TX (US)

(73) Assignee: Sovereign Pharmaceuticals, LLC, Fort Worth, TX (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/148,947

(22) Filed: Jan. 7, 2014

Related U.S. Application Data

(63) Continuation of application No. 11/672,075, filed on Feb. 7, 2007, now Pat. No. 8,653,135.

(51) Int. Cl.
*A01N 37/12* (2006.01)
*A01N 37/44* (2006.01)
*A61K 31/195* (2006.01)
*A61K 31/137* (2006.01)
*A61K 45/06* (2006.01)

(52) U.S. Cl.
CPC ............... *A61K 31/137* (2013.01); *A61K 45/06* (2013.01)

(58) Field of Classification Search
USPC ....................................................... 514/561
See application file for complete search history.

(56) References Cited

U.S. PATENT DOCUMENTS

| 4,401,665 | A | 8/1983 | Sheinaus et al. |
| 5,073,380 | A | 12/1991 | Babu et al. |
| 5,681,577 | A | 10/1997 | Lech et al. |
| 6,979,689 | B2 | 12/2005 | Gonzales et al. |
| 2005/0232986 | A1 | 10/2005 | Brown et al. |
| 2005/0232987 | A1 | 10/2005 | Srinivasan et al. |
| 2005/0232993 | A1 | 10/2005 | Brown et al. |
| 2005/0266032 | A1 | 12/2005 | Srinivasan et al. |
| 2005/0281875 | A1 | 12/2005 | Srinivasan et al. |
| 2006/0029664 | A1 | 2/2006 | Srinivasan et al. |
| 2006/0057205 | A1 | 3/2006 | Srinivasan et al. |
| 2006/0134207 | A1 | 6/2006 | Srinivasan et al. |
| 2007/0003622 | A1 | 1/2007 | Srinivasan et al. |

OTHER PUBLICATIONS

Lednicky et al. (Current Opinion in Pulmonary Medicine. 2006; 12: 235-239).*
U.S. Appl. No. 11/059,666, filed Feb. 17, 2005 and entitled "Bronchitis Medicine".
U.S. Appl. No. 11/132,300, filed May 19, 2005 and entitled "Pharmaceutical dosage form for treating rhinorrhea".

* cited by examiner

*Primary Examiner* — Kathrien Cruz
(74) *Attorney, Agent, or Firm* — Abel Law Group LLP

(57) ABSTRACT

A combination of dosage units for alleviating respiratory ailments and a method of alleviating respiratory ailments which uses this combination of dosage units. The dosage units comprise one or more first dosage units comprising pseudoephedrine and/or a pharmaceutically acceptable salt thereof and one or more second dosage units comprising phenylephrine and/or a pharmaceutically acceptable salt thereof.

20 Claims, No Drawings

ALTERNATING SYMPATHOMIMETIC THERAPY FOR THE TREATMENT OF RESPIRATORY AILMENTS

CROSS-REFERENCE TO RELATED APPLICATIONS

The present application is a continuation of application Ser. No. 11/672,075, filed Feb. 7, 2007, the entire disclosure of which is expressly incorporated by reference herein.

BACKGROUND OF THE INVENTION

1. Field of the Invention

The present invention relates to a combination of dosage units for alleviating/treating respiratory ailments such as nasal congestion and to a method of alleviating/treating respiratory ailments which uses this combination of the dosage units. The dosage units comprise one or more first dosage units comprising a first sympathomimetic agent, i.e., pseudoephedrine and/or a pharmaceutically acceptable salt thereof, and one or more second dosage units comprising a second sympathomimetic agent, i.e., phenylephrine and/or a pharmaceutically acceptable salt thereof.

2. Discussion of Background Information

Pseudoephedrine and its pharmaceutically acceptable salts are powerful symapthomimetic agents used for the control of allergic manifestations and for decongestion of respiratory airways in human subjects. However, pseudoephedrine containing products often give rise to excessive plasma concentrations when ingested according to dosage directions. These levels can reach blood concentrations that are 75% to 200% higher than the concentration needed for therapeutic effects.

Current dosage schedules of pseudoephedrine containing products available in the United States contain labels that instruct adult patients to ingest a maximum dosage of 60 mg of immediate release pseudoephedrine hydrochloride or other pharmaceutically acceptable salts thereof every 4 to 6 hours, but not to exceed 240 mg in a 24 hour period. Sustained release oral dosage forms of pseudoephedrine instruct an adult person to ingest 120 mg per dose every 12 hours, or 240 mg per dose in case of a 24 hour dosage form.

Regardless of whether the ingested dosage form is an immediate or a controlled release dosage form, at the end of the dosage cycle the plasma concentration of pseudoephedrine will still be above or barely below the therapeutic level, since the half life of pseudoephedrine is about 6 to 8 hours. Accordingly, it is inevitable that the second and all subsequent doses will exceed the minimum therapeutic plasma concentration by 75% to 200%, depending on whether the dosage is taken every 4 hours or every 6 hours or is taken in the form of a controlled release dosage unit.

There is no question that excessive therapeutic levels of pseudoephedrine of the order of 75% to 200% will more likely provoke the known side effects thereof such as, e.g., cardiovascular stimulation with elevated blood pressure, tachycardia or arrhythmias, central nervous system stimulation with resulting nervousness, excitability, restlessness, dizziness, weakness, insomnia, anxiety, tremors, hallucinations, skin rashes, urinary retention, headache and drowsiness. Large doses of pseudoephedrine may also cause lightheadedness, nausea and/or vomiting. Pseudoephedrine may further increase the irritability of the heart muscle and may alter the rhythmic function of the ventricles, especially in large doses or when administered to patients who are hypersensitive to the myocardial effects of sympathomimetic drugs.

A way to prevent excessive plasma concentrations of pseudoephedrine would be to allow the blood levels of pseudoephedrine to fall low enough so that the second and subsequent dosages do not add excessive amounts of the agent into the blood stream. However, this solution appears contrary to both precedent and conventional medical practice, since it would leave the patient suffering from respiratory ailments relating to allergies, common colds, or other common types of respiratory ailments for which sympathomimetics are indicated without adequate medication for several hours each day.

In view of the foregoing, there is a need to avoid excessive plasma concentrations of pseudoephedrine during the continued administration of pseudoephedrine dosage forms without interrupting the therapeutic effect provided by pseudoephedrine.

SUMMARY OF THE INVENTION

The present invention provides a combination of oral dosage units for alleviating respiratory ailments such as nasal congestion. The combination comprises one or more first dosage units which comprise pseudoephedrine and/or a pharmaceutically acceptable salt thereof and one or more second dosage units which comprise phenylephrine and/or a pharmaceutically acceptable salt thereof. At least one of the first and second dosage units comprises an antihistamine and/or is free of an expectorant and/or is free of a cough suppressant.

In one aspect of the combination, the first and/or the second dosage units may comprise at least one additional active ingredient such as, e.g., an antihistamine and/or a cough suppressant, and/or an expectorant, and/or an analgesic and/or an anti-inflammatory agent. For example, one or both of the first and second dosage units may comprise one or more antihistamines and/or one or both of the first and second dosage units may comprise one or more cough suppressants.

In another aspect of the combination, the first and second dosage units may each independently comprise an antihistamine and/or a cough suppressant and/or an expectorant and/or an analgesic and/or an anti-inflammatory agent. By way of non-limiting example, both the first and second dosage units may comprise an antihistamine and/or a cough suppressant, or one of the first and second dosage units may comprise an antihistamine and the other one of the first and second dosage units may comprise a cough suppressant. Particularly, at least the first dosage unit may comprise one or more antihistamines and at least the second dosage unit may comprise one or more cough suppressants.

In yet another aspect of the combination of the present invention, the first dosage units may further comprise one or more additional active ingredients which are selected from chlorpheniramine, promethazine, carbetapentane, codeine and pharmaceutically acceptable salts thereof and/or the second dosage units may further comprise one or more additional active ingredients which are selected from chlorpheniramine, dexchlorpheniramine, carbinoxamine, hydrocodone, codeine, guaifenesin and pharmaceutically acceptable salts thereof.

In a still further aspect of the combination of the present invention, a single first dosage unit may comprise from about 90 mg to about 150 mg of pseudoephedrine hydrochloride or an equivalent amount (in terms of moles of base compound) of pseudoephedrine and/or another pharmaceutically acceptable salt thereof and/or a single second dosage unit may comprise from about 20 mg to about 40 mg of phenylephrine hydrochloride or an equivalent amount (in terms of moles of base compound) of phenylephrine and/or another pharmaceutically acceptable salt thereof. For example, a single first dosage unit may comprise from about 100 mg to about 140 mg of pseudoephedrine hydrochloride or an equivalent amount of pseudoephedrine and/or another pharmaceutically acceptable salt thereof, and a single second dosage unit may comprise from about 25 mg to about 35 mg of phenylephrine or an equivalent amount of phenylephrine and/or another pharmaceutically acceptable salt thereof.

In another aspect of the combination, the first and second dosage units may independently comprise tablets, capsules, powders, solutions, suspensions, gels and syrups. For example, the first and second dosage units may both comprise suspensions or the first and second dosage units may both comprise tablets such as, e.g., multilayered (for example, bi-layered) tablets.

In another aspect of the combination, the first and/or the second dosage units may comprise a controlled release formulation and/or the first and/or the second dosage units may comprise an immediate release formulation.

In yet another aspect of the combination, the first and/or the second dosage units may comprise multilayered tablets. For example, the first and second dosage units may both comprise multilayered tablets, e.g., bi-layered tablets. For example, a multilayered tablet of the first dosage unit may comprise a first layer which is an immediate release layer and a second layer which is a controlled release layer and/or a multilayered tablet of the second dosage unit may comprise a first layer which is an immediate release layer and a second layer which is a controlled release layer.

In another aspect, the first (immediate release) layer of a multilayered tablet of the first dosage unit may comprise an antihistamine and/or a multilayered (e.g., bi-layered or tri-layered) tablet of the second dosage unit may comprise two different controlled release layers. For example, at least one of the two controlled release layers may comprise a cough suppressant.

In another aspect of the present invention, the combination may be a packaged combination which may comprise the first dosage units contained in at least one first container and the second dosage units contained in at least one second container.

In yet another aspect of the present invention, the combination may further comprise instructions directing ingestion of the first dosage units prior to periods during which a subject intends to be awake (also referred to herein as "daytime administration") and ingestion of the second dosage units prior to periods during which a subject intends to sleep (also referred to herein as "nighttime administration").

The present invention further provides a regimen for the alleviation of respiratory ailments such as nasal congestion. The regimen comprises the administration to a subject in need thereof of one or more first dosage units which comprise pseudoephedrine and/or a pharmaceutically acceptable salt thereof in an amount which is sufficient to maintain a therapeutically effective plasma level of pseudoephedrine for a first period, and subsequently the administration to the subject of one or more second dosage units which comprise phenylephrine and/or a pharmaceutically acceptable salt thereof in an amount which is sufficient to maintain a therapeutically effective plasma level of phenylephrine for a second period. The first and second dosage units are administered such that there is substantially no time gap between the first and second periods.

In one aspect of the regimen, there may be substantially no overlap between the first and second periods.

In another aspect of the regimen, the first and the second periods together may be about 24 hours long and/or the first period may be from about 12 hours to about 16 hours long.

In yet another aspect of the regimen, a one-time administration of the one or more first dosage units may be sufficient to maintain a therapeutically effective plasma level of pseudoephedrine over the entire first period and/or a one-time administration of the one or more second dosage units may be sufficient to maintain a therapeutically effective plasma level of phenylephrine over the entire second period.

In a still further aspect of the regimen, the first period may substantially coincide with the period during which the subject intends to be awake, and the second period may substantially coincide with a period during which the subject intends to be asleep.

In yet another aspect, the administration of the first dosage unit and the subsequent administration of the second dosage unit may be repeated at least once.

In another aspect of the regimen, the minimum therapeutically effective plasma level of pseudoephedrine may not substantially be exceeded over the entire first period.

In yet another aspect of the regimen of the present invention, the first and/or the second dosage units may further comprise at least one additional active ingredient such as, e.g., an antihistamine and/or a cough suppressant and/or an expectorant and/or an analgesic and/or an anti-inflammatory agent.

In another aspect of the regimen, the period of the therapeutic plasma level of the at least one additional active ingredient may overlap with at least about 70% of the first period or the second period, respectively.

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description making apparent to those skilled in the art how the several forms of the present invention may be embodied in practice.

The present invention provides a combination which comprises one or more first dosage units comprising pseudoephedrine and/or a pharmaceutically acceptable salt thereof and one or more second dosage units comprising phenylephrine and/or a pharmaceutically acceptable salt thereof.

The combination of the present invention generally minimizes or at least substantially reduces the side effects associated with the administration of pseudoephedrine by avoiding overdosing of pseudoephedrine caused by second and subsequent intakes. The present invention addresses the problem of overdosing pseudoephedrine by administering phenylephrine in substantially alternating order, which allows the pseudoephedrine plasma concentration to fall low enough so that the subsequent administration of pseudoephedrine does not cause an excessive plasma concentration of pseudoephedrine, i.e., a concentration which is significantly higher than the minimum therapeutically effective plasma concentration, and at the same time allows to maintain the needed therapeutic relief by providing the sympathomimetic agent phenylephrine.

Phenylephrine is a powerful sympathomimetic agent recognized by the Federal Food and Drug Administration as effective for the treatment of the same medical indications as pseudoephedrine (it is related to the most effective anti-allergic sympathomimetic agent available—epinephrine—known by its trade name 'adrenalin'—whereas pseudoephedrine is related to ephedrine). Phenylephrine actually slows the heart rate, when given in adequate dosages. This action is diametrically opposed to the increase in heart rate associated with adverse effects of pseudoephedrine. Phenylephrine also has a much shorter therapeutic half-life than pseudoephedrine—only about 2½ hours—so the elimination of this agent from the blood stream occurs much more rapidly after the levels fall below therapeutic levels and for this reason an excessive build-up of this sympathomimetic agent in the blood stream is prevented when the alternate pseudoephedrine dosage is ingested.

The first and second dosage units of the combination of the present invention may comprise additional active ingredients such as, e.g., antihistamines, cough suppressants, expectorants, analgesics and anti-inflammatory agents. The additional active ingredients may be present independently in both the first and second dosage units or in only one of these dosage units. For example, the first dosage units may comprise one or more additional active ingredients and the second dosage units may comprise one or more additional active ingredients. The one or more additional active ingredients in the first dosage units may be the same as or different from the one or more additional active ingredients in the second dosage units. Also, the additional active ingredients in the first and second dosage units may partially overlap. By way of non-limiting example, the first dosage units may comprise a first additional active ingredient and a second additional active ingredient and the second dosage units may comprise a first additional active ingredient and a second additional active ingredient. In this case the first and second additional active ingredients of the first dosage units and the first and second additional active ingredients of the second dosage units may be the same or different. Alternatively, the first additional active ingredients of the first and second dosage units may be the same and the second additional ingredients of the first and second dosage forms may be different from each other. Of course, these are but a few examples of combinations of active ingredients that may be present in the first and second dosage units.

The antihistamines, expectorants, cough suppressants, analgesics and anti-inflammatory agents which may be comprised in the combination of the present invention may be selected from a wide variety of active ingredients. For example, non-limiting examples of suitable antihistamines include astemizole, azatadine, azelastine, bromodiphenhydramine, brompheniramine, carbinoxamine, cetirizine, chlorcyclizine, clemastine, chlorothen, chlorpheniramine, cyclizine, cyproheptadine, desloratadine, dexbrompheniramine, dimethindene, diphenhydramine, diphenylpyraline, doxylamine, fexofenadine, hydroxyzine, isothipendyl, loratadine, methapyrilene, montelukast, phenindamine, pheniramine, phenyltoloxamine, promethazine, prophenpyridamine, pyrilamine, terfenadine, thenyldiamine, thonzylamine, trimeprazine, tripelennamine, triprolidine and pharmaceutically acceptable salts thereof such as, e.g., zatadine maleate, bromodiphenhydramine HCl, brompheniramine maleate, carbinoxamine maleate, cetirizine HCl, chlorcyclizine HCl, clemastine fumarate, chlorothen citrate, chlorpheniramine maleate, dimethindene maleate, diphenhydramine HCl, fexofenadine HCl, hydroxyine HCl, isothipendyl HCl (theruhistin), methapyrilene fumarate, methapyrilene HCl, montelukast sodium, phenindamine tartrate, pheniramine maleate, phenyltoloxamine citrate, promethazine hydrochloride, prophenpyridamine maleate, pyrilamine maleate, thenyldiamine HCl, trimeprazine tartrate, tripelennamine HCl and triprolidine HCl.

Non-limiting examples of cough suppressants include, e.g., codeine, dihydrocodeine, hydrocodone, hydromorphone, dextromethorphan, carbetapentane, chlophedianol, benzonatate, caramiphen, noscapine and pharmaceutically acceptable salts thereof such as, e.g., codeine phosphate, codeine sulfate, hydrocodone bitartrate, dihydrocodeine bitartrate, carbetapentane citrate and dextromethorphan hydrobromide.

Non-limiting examples of expectorants (including mucus thinning drugs) include guaifenesin and pharmaceutically acceptable salts thereof.

Non-limiting examples of analgesic and/or anti-inflammatory agents include aspirin, acetaminophen, ibuprofen, ketoprofen, naproxen, sodium naproxen, meloxicam, hydrocodone, oxycodone, morphine, meperidine, and fentanyl.

The term "pharmaceutically acceptable salts" as used herein refers to those salts of a particular active ingredient that are not substantially toxic at the dosage administered to achieve the desired effect and do not independently possess significant pharmacological activity. The salts included within the scope of this term are pharmaceutically acceptable acid addition salts of a suitable inorganic or organic acid. Non-limiting examples of suitable inorganic acids are, for example hydrochloric, hydrobromic, sulfuric and phosphoric acids. Non-limiting examples of suitable organic acids include carboxylic acids, such as acetic, propionic, tannic, glycolic, lactic, pyruvic, malonic, succinic, fumaric, malic, tartaric, citric, cyclamic, ascorbic, maleic, hydroxymaleic, benzoic, phenylacetic, 4-aminobenzoic, 4-hydroxybenzoic, anthranillic, cinnamic, salicylic, 4-aminosalicyclic, 2-phenoxybenzoic, 2-acetoxybenzoic and mandelic acids, as well as sulfonic acids, such as methanesulfonic, ethanesulfonic, and β-hydroxyethanesulfonic acids.

The optional additional active ingredients of the first and second dosage units may vary between separate first dosage units. The same applies with respect to the presence of additional active ingredients for the second dosage units. In other words, the first (second) dosage units may not all be the same and may differ, except that pseudoephedrine is always included in the first dosage units and phenylephrine in the second dosage units. However, to simplify administration it will usually be preferred to provide a single first dosage unit (e.g., a tablet, capsule, suspension, etc.) that contains all of the first active ingredients as well as a single second dosage unit (e.g., a tablet, capsule, suspension, etc.) that contains all of the second active ingredients.

The first dosage unit(s) and the second dosage unit(s) of the combination of the present invention are adapted for oral administration. The dosage forms for the first and second dosage unit(s) may be a solid form, for example, a dosage form selected from tablets, capsules, pills, caplets, powders and lozenges, or the first/second dosage unit(s) may comprise a liquid or semi-liquid dosage form such as, e.g., a solution, a suspension, a syrup, or a gel. The dosage form of the first dosage unit(s) and the dosage form of the second dosage unit(s) may be the same or may be different. By way of non-limiting example, the first and second dosage unit(s) may both be present in solid form, e.g., in the form of a tablet (e.g., a multilayered tablet), or the first and second dosage unit(s) may both be present in liquid form, e.g., in the form of a suspension. Also, the first (second) dosage unit(s) may be present in solid form, e.g., as a tablet, and the second (first) dosage unit(s) may be present in liquid form, e.g., as a syrup.

The active ingredients contained in the first and second dosage units may be present in an immediate release dosage form and/or they may be present in a controlled release dosage form. The term "controlled release dosage form" as used herein and in the appended claims includes any dosage form that is not an immediate release dosage form, i.e., does not release the active ingredient contained therein within a relatively short period of time (for example, within less than about 1 hour, e.g., less than about 0.5 hours following ingestion of the dosage form). Accordingly, this term is a generic term which encompasses, e.g., sustained (extended) release dosage forms, pulsed release dosage forms, delayed release dosage forms, and the like. Preferably, the controlled release dosage forms release the one or more active ingredients contained therein continuously or intermittently and, preferably, in approximately equal amounts per time unit, over an extended period of time such as, e.g., at least about 4 hours, at least about 6 hours, at least about 8 hours, at least about 10 hours, at least about 12 hours, at least about 14 hours, or at least about 16 hours. The desirable length of time period of continuous or intermittent (e.g., pulsed) release depends, inter alia, on the plasma half-life of the active ingredient and/or an active metabolite thereof.

It is to be appreciated that each of the first (second) dosage units may comprise immediate release dosage forms and controlled release dosage forms at the same time. The same applies to the simultaneous presence of two or more different controlled release dosage forms in the first (second) dosage units. Different dosage forms can be present in different dosage units or may be combined in a single dosage unit such as, a multilayered tablet, preferably, a bi-layered tablet. Non-limiting examples of further suitable dosage units and of other optional and/or preferred features of the combination of the present invention are set forth in, e.g., copending U.S. application Nos. 2005/0232986 A1, 2005/0232987 A1, 2006/0029664 A1, 2006/0057205 A1, 2006/0134207 A1, 2005/0281875 A1, 2007/0003622 A1, 2005/0266032 A1 and 2005/0232993 A1, the entire disclosures whereof are expressly incorporated by reference herein.

For example, a multi-layered tablet for use in the present invention will comprise at least a first layer and a second layer, but may optionally comprise a third, fourth, fifth, etc. layer. The first layer may be an immediate release layer or a controlled release layer, depending on the active ingredient(s) contained therein and the desired release characteristics thereof. The second layer may also be an immediate release layer or a controlled release layer, depending on the active ingredient(s) contained therein and the desired release characteristics thereof. If more than two active ingredients are to be incorporated in the tablet, the first and/or the second layer may contain all of the active ingredients. Alternatively, separate additional layers may be provided for the additional active ingredient(s), for example, in cases where it would be difficult to design a controlled release layer which provides a desired release rate for different active ingredients. Of course, a fourth, fifth, etc. layer may be provided for, e.g., a third or fourth additional active ingredient, and so on. Alternatively and by way of non-limiting example, the second and a third layer may contain the same active ingredient(s), but in different (relative) concentrations and/or incorporated in a different controlled release formulation.

A multi-layered tablet for use in the combination of the present invention will usually be made up of two or more distinct layers or discrete zones of granulation compressed together with the individual layers lying on top of one another. Layered tablets have the appearance of a sandwich because the edges of each layer or zone are exposed. Such conventional layered tablets are generally prepared by compressing a granulation onto a previously compressed granulation. The operation may be repeated to produce multilayered tablets with more than two layers.

It is to be noted that it is not necessary for the two or more individual layers of the multilayered tablet to lie on top of one another. By way of non-limiting example, a second layer (e.g., sustained release layer) may be partially or completely surrounded by a first layer (e.g., an immediate release layer). For example, the second layer may be coated with the first layer. In the case of three layers, for example, the third layer may be partially or completely coated with the second layer, which in turn may be partially or completely coated with the first layer. Of course, these are but a few examples of the many different ways in which the various layers of a multilayered tablet for use in the combination of the present invention can be arranged relative to each other. Moreover, it is to be understood that tablets for use in the present invention are not limited to multilayered tablets. By way of non-limiting example, the tablet may comprise an immediate release matrix which comprises one or more first active ingredients, which matrix has dispersed therein particles of one or more sustained release formulations which have one or more active ingredients (which may the same or different from those in the immediate release matrix) incorporated therein.

The simultaneous use of different dosage forms, e.g., immediate release and extended release dosage forms, for the first (second) dosage units may, for example, be particularly advantageous in cases where one or more of the active ingredients have a plasma half-life that differs significantly (e.g., by several hours) from the plasma half-life of one or more of the other active ingredients that are present in the first (second) dosage units. By using a different release profile for active ingredients with significantly different plasma half-life it is possible to ensure that these active ingredients exhibit their therapeutic effects over similar time periods.

The first and second layers of a dosage unit such as a bi-layered tablet for use in the combination of the present invention will usually contain the pseudoephedrine or phenylephrine and the optional additional active ingredient(s) contained therein in amounts which are commensurate with the intended duration of action but will not give rise to over-dosing when present in the intended form (e.g., a particular pharmaceutically acceptable salt) and the intended release matrix (e.g., immediate release, controlled release, etc.). In this regard, it is noted that any active ingredient may be present in both the first layer and the second layer (and any additional layer, if present), for example, in order to obtain an as fast as possible release and, thus action of the active ingredient (e.g., by using an immediate release matrix) and to at the same time extend the duration of the action of the active ingredient (e.g., by using a controlled release matrix that releases the drug at a lower rate and/or at a later time than the immediate release layer). In the following, preferred ranges of amounts of selected active ingredients for use in a bi-layered tablet or any other dosage form for use in the combination of the present invention are given for illustrative purposes only.

Promethazine: at least about 0.1 mg, e.g., at least about 5 mg, at least about 6 mg, at least about 8 mg, at least about 12 mg, or at least about 25 mg, but not more than about 90 mg, e.g., not more than about 75 mg, not more than about 70 mg, not more than about 60 mg, or not more than about 50 mg of promethazine hydrochloride or an equivalent amount (on a molar basis) of promethazine and/or any other pharmaceutically acceptable salt thereof.

Chlorpheniramine: at least about 0.1 mg, e.g., at least about 2 mg, or at least about 4 mg, but not more than about 16 mg, e.g., not more than about 12 mg of chlorpheniramine maleate or an equivalent amount of chlorpheniramine and/or any other pharmaceutically acceptable salt thereof.

Carbinoxamine: at least about 0.1 mg, e.g., at least about 6 mg, but not more than about 32 mg, e.g., not more than about 24 mg of carbinoxamine maleate or an equivalent amount of carbinoxamine and/or any other pharmaceutically acceptable salt thereof.

Diphenhydramine: at least about 10 mg, e.g., at least about 15 mg, at least about 20 mg, at least about 40 mg, at least about 70 mg, or at least about 90 mg, but not more than about 200 mg, e.g., not more than about 150 mg, not more than about 120 mg, or not more than about 100 mg of diphenhydramine hydrochloride or an equivalent amount of diphenhydramine and/or any other pharmaceutically acceptable salt thereof.

Carbetapentane: at least about 1 mg, e.g., at least about 5 mg, at least about 10 mg, at least about 25 mg, or at least about 50 mg, but not more than about 120 mg, e.g., not more than about 100 mg, not more than about 70 mg, or not more than about 60 mg, of carbetapentane citrate or an equivalent amount of carbetapentane and/or any other pharmaceutically acceptable salt thereof.

Codeine: at least about 1 mg, e.g., at least about 10 mg, at least about 25 mg, or at least about 30 mg, but not more than about 120 mg, e.g., not more than about 80 mg, not more than about 60 mg, or not more than about 45 mg, of codeine phosphate or an equivalent amount of codeine and/or any other pharmaceutically acceptable salt thereof.

Dihydrocodeine: at least about 1 mg, e.g., at least about 5 mg, but not more than about 30 mg, e.g., not more than about 20 mg, of dihydrocodeine bitartrate or an equivalent amount of dihydrocodeine and/or any other pharmaceutically acceptable salt thereof.

Hydrocodone: at least about 1 mg, e.g., at least about 5 mg, but not more than about 20 mg, e.g., not more than about 15 mg, of hydrocodone bitartrate or an equivalent amount of hydrocodone and/or any other pharmaceutically acceptable salt thereof.

Guaifenesin: at least about 1 mg, e.g., at least about 10 mg, at least about 25 mg, at least about 50 mg, or at least about 100 mg, but not more than about 2400 mg, e.g., not more than about 1600 mg, not more than about 1500 mg, not more than about 1200 mg, not more than about 1000 mg, not more than about 600 mg, or not more than about 500 mg of guaifenesin or an equivalent amount of a pharmaceutically acceptable salt thereof.

Acetaminophen: at least about 10 mg, e.g., at least about 50 mg, or at least about 100 mg, but not more than about 1000 mg, e.g., not more than about 500 mg, or not more than about 250 mg of acetaminophen.

In a preferred aspect of the combination of the present invention, the one-time ingestion of one of the first and second dosage units provides relief from the symptoms associated with respiratory ailments such as, e.g., nasal congestion for a period until it is time to take the other one of the first and second dosage units. In other words, both the first and second dosage units are preferably capable of providing therapeutically effective plasma concentrations of the active ingredients contained therein over extended periods of time, for example, for the first dosage units at least about 10 hours, at least about 12 hours, at least about 14 hours or at least about 16 hours, and for the second dosage units at least about 8 hours, at least about 10 hours, or at least about 12 hours.

A preferred single first dosage unit (or a plurality of dosage units to be ingested at once) will comprise a total of at least about 50 mg, e.g., at least about 60 mg, at least about 75 mg, at least about 80 mg, at least about 100 mg, or at least about 120 mg, but not more than about 150 mg, not more than about 140 mg, or not more than about 130 mg of pseudoephedrine hydrochloride or an equivalent amount of pseudoephedrine and/or any other pharmaceutically acceptable salt thereof (e.g., pseudoephedrine tannate).

A preferred second dosage unit (or a plurality of second dosage units to be ingested at once) will comprise a total of at least about 20 mg, e.g., at least about 30 mg, at least about 40 mg, at least about 50 mg, at least about 60 mg, at least about 75 mg, but not more than about 90 mg, e.g., not more than about 85 mg or not more than about 80 mg of phenylephrine hydrochloride or an equivalent amount of phenylephrine and/or another pharmaceutically acceptable salt thereof (e.g., phenylephrine tannate).

The dosage units of the combination of the present invention can be manufactured by processes which are well known to those of skill in the art. For example, for the manufacture of tablets the active ingredients may be dispersed uniformly into a mixture of excipients, for example, by high shear granulation, low shear granulation, fluid bed granulation, or by blending for direct compression.

Excipients may include diluents, binders, disintegrants, dispersants, lubricants, glidants, stabilizers, surfactants and colorants. Diluents, also termed "fillers", are typically used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders impart cohesive qualities to a tablet formulation and are used to ensure that a tablet remains intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants facilitate tablet manufacture; non-limiting examples thereof include magnesium stearate, calcium stearate, stearic acid, glyceryl behenate, and polyethylene glycol. Disintegrants facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc and the like. Stabilizers inhibit or retard drug decomposition reactions, including oxidative reactions. Surfactants may be anionic, cationic, amphoteric or nonionic. If desired, the tablets may also contain minor amounts of nontoxic auxiliary substances such as pH buffering agents, preservatives, e.g., antioxidants, wetting or emulsifying agents, solubilizing agents, coating agents, flavoring agents, and the like.

Extended/sustained release formulations may be made by choosing the right combination of excipients that slow the release of the active ingredients by coating or temporarily bonding or decreasing the solubility of the active ingredients. Examples of these excipients include cellulose ethers such as hydroxypropylmethylcellulose (e.g., Methocel K4M), polyvinylacetate-based excipients such as, e.g., Kollidon SR, and polymers and copolymers based on methacrylates and methacrylic acid such as, e.g., Eudragit NE 30D.

Several commercially available tablet presses are capable of making tablets for use in the combination of the present invention. For example, Manesty RotaPress Diamond, a 45 D tooling press, is capable of making bi-layered tablets. Non-limiting examples of presses for the manufacture of tablets include Fette America Model No. PT3090; Maneklal Global Exports Models JD and DH series (Mumbai, India); Niro Pharma Systems, Model R292F; and Korsch AG Models XL 800 and XL400.

The one or more first dosage units and the one or more second dosage units of the combination of the present invention are preferably held in separate dispensing containers which in turn are preferably accommodated in a single dispensing unit such as, e.g., a small box of the type that is conventionally used for medicine that is sold over the counter. Of course, the single dispensing unit may also take other forms such as, e.g., a plastic bag that contains two or more dispensing containers. In another non-limiting embodiment, the dispensing containers may be held together by a plastic film such as, e.g., a shrink-wrap film.

The dispensing containers for the first and second dosage units of the combination of the present invention may take various forms, for example, conventional forms for pharmaceutical containers such as, e.g., bottles, tubes, pouches, canisters and packets. Preferred, non-limiting examples of dispensing containers include bottles and blister packages. Preferably, but not necessarily, the first and second dosage units will be provided in the same type of dispensing container such as, e.g., in a first bottle which accommodates the first dosage units and in a second bottle which accommodates the second dosage units. It may sometimes be desirable to provide more than one dispensing container for each type of dosage unit (mainly depending on the quantity and size of the dosage units to be provided in a single dispensing unit).

The first and second dosage units of the combination of the present invention will usually and preferably be rendered easily distinguishable. Especially in the case of solid dosage forms such as, e.g., tablets, pills, capsules and the like, a convenient way of making the first and second dosage units distinguishable is by providing them with a different color (e.g., yellow and blue) or a different shade, brightness, etc. of the same color (e.g., a lighter color tone for daytime administration and a darker color tone for nighttime administration). Of course, one of skill in the art will be aware of many other ways that are suitable for rendering the different dosage units distinguishable, for example, different sizes, different shapes, different indicia, different dosage forms (e.g., solid and liquid), etc. Also, two or more different ways of making the dosage units distinguishable may be combined.

Alternatively or cumulatively, the dosage units may be made distinguishable through the dispensing containers that accommodate them. As in the case of the dosage units themselves, the colors, shapes, sizes and types of the dispensing containers are non-limiting features thereof which provide particularly convenient means for making them readily distinguishable.

Also, a dispensing container for the first dosage units and a dispensing container for the second dosage units may have different indicia thereon. The use of different indicia is advantageous in that it not only allows making the different dosage units distinguishable but also provides a way of clearly and unambiguously indicating whether the dosage units are intended for daytime administration or for nighttime administration (e.g., by providing them with words such as "DAY" or "NIGHT" thereon). Of course, the dispensing containers may have additional information thereon, for example, information which identifies the particular day of the treatment regimen for which a given dosage unit is intended (e.g., "DAY 1", "DAY 2", etc.).

In addition to the first and second dosage units, the optional dispensing containers and the optional dispensing unit which accommodates the containers, the combination of the present invention may comprise further components. In particular, the first and second dosage units are preferably accompanied by instructions (e.g., labels) which instruct the patient as to which dosage units are to be taken for daytime and which dosage units are to be taken for nighttime. Corresponding instructions will preferably also provide information as to how many dosage units are to be taken at a time (e.g., one dosage unit for children and two dosage units for adults, etc.), and in which intervals. Further, the instructions may provide information as to the recommended number of days for which the dosage units should be ingested.

The present invention also provides a regimen for the alleviation of repiratory ailments such as nasal congestion wherein the one or more first dosage units are administered to a subject in need thereof in an amount which is sufficient to maintain a therapeutically effective plasma level of pseudoephedrine over a first period, and wherein the one or more second dosage units are administered to the subject in an amount which is sufficient to maintain a therapeutically effective plasma level of phenylephrine over a second period.

The first period of the regimen of the present invention substantially coincides with a period during which the subject intends to be awake (usually during the day, hereafter frequently referred to as being suitable/desirable "for daytime administration", although it is to be appreciated that, for example, some people work during the night and sleep during the day wherefore they would have to take the first dosage units for the nighttime period). The first dosage units for the first period are preferably free of any substance that causes drowsiness in a (human) patient.

The second period of the regimen coincides with a period during which the patient intends to sleep (usually at least during the night, hereafter frequently referred to as being suitable/desirable "for nighttime administration", although it is to be appreciated that, for example, some people work during the night and sleep during the day wherefore the would have to take the second dosage units for the daytime period. The second dosage units for the second period are preferably free of any substance that causes nervous system stimulation in a (human) patient.

Preferably, the regimen of the present invention is designed so that there is substantially no overlap or gap between the first and second periods. For example, the first period will usually not overlap the second period by more than about 30 minutes, e.g., not more than about 15 minutes, or not more than about 10 minutes. Also, a time gap between the first and second periods will usually be not longer than about 30 minutes, e.g., not longer than about 15 minutes or not longer than about 10 minutes. Preferably, the first period and the second period together are about 24 hours long, wherein, in a preferred aspect, the first period is from about 12 hours to about 16 hours long.

In the regimen, preferably a one-time administration of the one or more first dosage units is sufficient to maintain a therapeutically effective plasma level of pseudoephedrine over the entire first period. A minimum therapeutically effective plasma level of pseudoephedrine is preferably not substantially exceeded with the regimen of the present invention. For example, the plasma level of pseudoephedrine provided by the regimen of the present invention will preferably not be higher than about 150%, e.g., not higher than about 125%, not higher than about 110%, or not higher than about 105% of the minimum therapeutically effective plasma level of pseudoephedrine. The same applies to the plasma level of phenylephrine. Also preferred is a one time administration of the one or more second dosage units to maintain a therapeutically effective plasma level of phenylephrine over the entire second period. Also in the case of phenylephrine the minimum therapeutically effective plasma level thereof is preferably not substantially exceeded with the regimen of the present invention. The administration of the one or more first dosage units and the subsequent administration of the one or more second dosage units is usually repeated at least once, e.g., at least 2 times, at least 3 times, at least 4 times and generally as many times as necessary for the symptoms of the respiratory ailments to subside.

In another aspect of the regimen of the present invention, the period for the at least one additional active ingredient comprised in the first and/or second dosage units overlaps with at least 70% of the first period or of the second period. In other words, the first and second dosage units which comprise one or more additional active ingredients are preferably designed to provide a plasma concentration within the therapeutic range of an additional active ingredient over a period which is coextensive with at least about 70% of the period over which the dosage units provide a plasma concentration within the therapeutic range of pseudoephedrine or phenylephrine, respectively. For example, with the dosage units of the present invention, the plasma concentration within the therapeutic range of an additional active ingredient may be coextensive with at least about 80%, e.g., at least about 90%, or at least about 95%, of the period of a plasma concentration within the therapeutic range of pseudoephedrine or phenylephrine. The term "therapeutic range" refers to the range of drug levels (including active metabolite levels) within which most patients will experience a significant therapeutic effect (including alleviation of symptoms) without an undesirable degree of adverse reactions. The "minimum therapeutically effective plasma level" is the minimum drug level (including active metabolite levels) within which most patients will experience a significant therapeutic effect (including alleviation of symptoms) without an undesirable degree of adverse reactions. It is noted that the term "coextensive with" does not exclude, but rather includes, cases where a part of the period over which the plasma concentration of a first drug (and/or active metabolites thereof) is within the therapeutic range is outside the period over which the plasma concentration of a second drug is within the therapeutic range.

The following non-limiting examples illustrate the present invention.

Example 1

A. Bi-Layered Tablet Comprising Pseudoephedrine for Day Time Administration

A bi-layered tablet which comprises pseudoephedrine tannate and chlorpheniramine tannate in an immediate release layer and carbetapentane tannate in a sustained release layer is illustrated as follows:

| Ingredients | Weight/tablet (mg) | Weight/1 kg batch (g) |
|---|---|---|
| Layer 1 (Immediate release) | | |
| Pseudoephedrine Tannate | 60.0 | 85.7 |
| Chlorpheniramine Tannate | 8.0 | 11.4 |
| Silicified Microcrystalline Cellulose | 108.0 | 154.3 |
| Povidone | 3.0 | 4.3 |
| Croscarmellose Sodium | 10.0 | 14.3 |
| Magnesium Stearate | 1.0 | 1.4 |
| Layer 2 (Sustained release) | | |
| Carbetapentane Tannate | 30.0 | 42.9 |
| Microcrystalline Cellulose (PH 102) | 30.0 | 42.9 |
| Lactose Monohydrate | 100.0 | 142.9 |
| Dicalcium Citrate | 100.0 | 142.9 |
| Povidone | 15.0 | 21.4 |
| Methocel K4M Premium | 210.0 | 300.0 |
| Stearic Acid | 20.0 | 28.6 |
| Magnesium Stearate | 5.0 | 7.1 |
| Total | 700.0 | 1000.0 |

Process:

(a) Immediate release layer #1: Pseudoephedrine tannate, chlorpheniramine tannate, silicified microcrystalline cellulose and croscarmellose sodium are mixed in a high shear mixer/granulator for 10 minutes. The resultant blend is granulated using a 30% povidone solution (3.0 g povidone in 10.0 g purified water). Upon completion of the granulation process, the wet mass is dried until the LOD (loss on drying) is less than 2.0% and the granules are screened through a USP sieve size #14. The granules and prescreened magnesium stearate are added to a V shaped blender and are mixed for 3 minutes.

(b) Sustained release layer #2: Carbetapentane tannate, microcrystalline cellulose PH 102, lactose monohydrate, dicalcium phosphate, Methocel K4M Premium and stearic acid are mixed in a high shear mixer/granulator for 10 minutes. The resultant blend is granulated using a 30% povidone solution (15.0 g povidone in 50.0 g purified water). Thereafter the granulation is dried until the LOD is less than 2.0% and the granules are screened through a USP sieve size #14. The granules and prescreened magnesium stearate are added in a V shaped blender and mixed for 3 minutes.

Bi-layered tablets are manufactured using a rotary bi-layer tablet press, wherein the weight of tablet layer #1 is about 190 mg and the weight of tablet layer #2 is about 510 mg. Capsules may be manufactured by filling the same proportions into capsules.

B. Bi-Layered Tablet Comprising Phenylephrine for Night Time Administration

A bi-layered tablet which comprises phenylephrine tannate and chlorpheniramine tannate in an immediate release layer and phenylephrine tannate in a sustained release layer is illustrated as follows:

| Ingredients | Weight/tablet (mg) | Weight/1 kg batch (g) |
|---|---|---|
| Layer 1 (Immediate release) | | |
| Phenylephrine Tannate | 60.0 | 60.0 |
| Chlorpheniramine Tannate | 8.0 | 8.0 |
| Silicified Microcrystalline Cellulose | 208.0 | 208.0 |
| Povidone | 3.0 | 3.0 |
| Croscarmellose Sodium | 10.0 | 10.0 |
| Magnesium Stearate | 1.0 | 1.0 |
| Layer 2 (Sustained release) | | |
| Phenylephrine Tannate | 30.0 | 30.0 |
| Microcrystalline Cellulose (PH 102) | 30.0 | 30.0 |
| Dicalcium Phosphate | 100.0 | 100.0 |
| Povidone | 15.0 | 15.0 |
| Methocel K4M Premium | 210.0 | 210.0 |
| Stearic Acid | 20.0 | 20.0 |
| Magnesium Stearate | 5.0 | 5.0 |
| Total | 700.0 | 700.0 |

Procedure:

(a) Immediate release layer #1: Phenylephrine tannate, chlorpheniramine tannate, silicified microcrystalline cellulose and croscarmellose sodium are mixed in a high shear mixer/granulator for 10 minutes. The resultant blend is granulated using a 30% povidone solution (3.0 kg povidone in 7.0 kg purified water). Upon completion of the granulation process, the wet mass is dried until the LOD is less than 2.0% and the granules are screened through a USP sieve size #14. Thereafter the granules and prescreened magnesium stearate are added to a V shaped blender and are mixed for 3 minutes.

(b) Sustained release layer #2: Phenylephrine tannate, microcrystalline cellulose PH 102, dicalcium phosphate, Methocel K4M Premium and stearic acid are mixed in a high shear mixer/granulator for 10 minutes. The obtained blend is granulated by using a 30% povidone solution (15.0 kg povidone in 35.0 kg purified water). Thereafter the wet mass is dried until the LOD is less than 2.0%, and the granules are screened through a US sieve size #14. The granules and prescreened magnesium stearate are added in a V shaped blender and mixed for 3 minutes.

Bi-layered tablets are manufactured by using a rotary bi-layer tablet press, wherein the amount of tablet layer #1 is about 290 mg and the amount of tablet layer #2 is about 410 mg. Capsules may be manufactured by filling the same proportions into capsules.

Example 2

A. Extended Release Suspension Comprising Pseudoephedrine for Day Time Administration An extended release suspension which comprises a codeine phosphate ion-exchange complex, pseudoephedrine tannate and chlorpheniramine tannate is illustrated as follows:

| Ingredients | Amount/5 ml |
| --- | --- |
| Codeine Phosphate Ion-Exchange Complex | Equivalent to 45 mg of Codeine Phosphate |
| Pseudoephedrine Tannate | 75.0 mg |
| Chlorpheniramine Tannate | 4.5 mg |
| Eudragit ® L 100 | 0.2 to 2.8 g |
| Silica, colloidal anhydrous, NF | 100 mg |
| Glycerin | 740 mg |
| Xylitol, NF | 800 mg |
| Sodium Citrate, USP | 100 mg |
| Saccharin Sodium cryst., USP, | 0.1 mg |
| Sodium Benzoate | 7.5 mg |
| Citric Acid Monohydrate, USP | 8.0 mg |
| Artificial Grape Flavor | 5 mg |
| FD&C Red # 40 Dye | 0.5 mg |
| Water | q.s |

Procedure for 1000 kg Batch:

Sodium polystyrene sulphonate USP (e.g. Amberlite® IRP 69) is added to a codeine phosphate solution and the mixture is stirred for 12 hours to allow complete drug/resin complex formation. Then the insoluble drug/resin complex is separated and dried. The drug/resin complex is granulated with a delayed release/enteric polymer (e.g. Eudragit® L 100, Kollidon® MAE, Aquacoat® CPD) and the granules are dried. If needed, the granules may be milled.

In a suitably sized stainless steel vessel saccharin sodium, sodium benzoate, citric acid, and sodium citrate are dissolved in approximately 50 L of warm (about 45° C.) purified water. In another large stainless steel drum silica, codeine phosphate ion-exchange complex, pseudoephedrine tannate and chlorpheniramine tannate are mixed until a uniform and consistent mixture is obtained. In a separate 1000 L stainless steel tank which is equipped with a suitably sized homogenizer/disperser about 100 L of purified water is added. With the homogenizer on, the silica mixture containing codeine phosphate ion-exchange complex, pseudoephedrine tannate and chlorpheniramine tannate is added to the stainless steel tank. Next, a previously prepared solution of saccharin sodium, sodium benzoate, citric acid, and sodium citrate is added to the tank. The first vessel is rinsed with about 2 L of water and the rinsate is transfered to the 1000 L tank. Finally, the remaining ingredients are added and homogenized for 15 minutes.

B. Extended Release Suspension Comprising Phenylephrine for Night Time Administration An extended release suspension which contains a hydrocodone bitartrate ion-exchange complex, a dexchlorpheniramine maleate ion-exchange complex and a phenylephrine hydrochloride ion-exchange complex is illustrated as follows:

| Ingredients | Amount/5 ml |
| --- | --- |
| Hydrocodone Bitartrate Ion-Exchange Complex | Equivalent to 8 mg of Hydrocodone Bitartrate |
| Dexchlorpheniramine Maleate Ion-Exchange Complex | Equivalent to 6 mg of Dexchlorpheniramine Maleate |
| Phenylephrine HCl Ion-Exchange Complex | Equivalent to 10 mg of Phenylephrine HCl |
| Eudragit ® L 100 | 0.2 to 2.8 g |
| Glycerin | 315 mg |
| Polysorbate 80 | 1.5 mg |
| Carbomer (e.g., Carbopol ® 974) | 15 mg |
| Methyl Paraben | 9 mg |
| Propyl Paraben | 1 mg |
| Artificial Grape Flavor | 5 mg |
| FD&C Red # 40 Dye | 0.5 mg |
| Water | q.s |

The formula described above serves as a non-limiting example. Any active drug which is in the form of a salt, such as an antihistamine, codeine, or dihydrocodeine, can be incorporated as an ion-exchange resin complex.

Procedure:

Sodium polystyrene sulphonate USP (e.g. Amberlite® IRP 69) is added to a solution of dexchlorpheniramine maleate, hydrocodone bitartrate and phenylephrine HCl and the mixture is stirred for 12 hrs to allow complete drug/resin complex formation. The resultant insoluble drug/resin complex is separated and dried. The drug/resin complex is granulated with a delayed release/enteric polymer (e.g. Eudragit® L 100, Kollidon® MAE, Aquacoat® CPD) and the granules are dried. If needed, the granules may be milled. Next, in an appropriate amount of water the following ingredients are dissolved: Carbomer (e.g., Carbopol® 974), glycerin, polysorbate 80, methyl paraben, propyl paraben, artificial grape flavor, FD&C red #40 dye. To this suspension the milled granules are added as well as more water to make up to a final volume. To avoid settling of the suspension and to maintain a homogeneous product mixture agitation at a suitable rate has to be maintained. The product is filled in suitable containers ensuring that the product is homogeneous throughout the filling operation.

Example 3

A. Extended Release Suspension Comprising Pseudoephedrine for Day Time Administration An extended release suspension which contains a carbetapentane citrate ion-exchange complex, pseudoephedrine tannate and chlorpheniramine tannate is illustrated as follows:

| Ingredients | Amount/5 ml |
|---|---|
| Carbetapentane Citrate Ion-Exchange Complex | Equivalent to 20 mg of Carbetapentane Citrate |
| Pseudoephedrine Tannate | 75.0 mg |
| Chlorpheniramine Tannate | 4.5 mg |
| Eudragit ® L 100 | 0.2 to 2.8 g |
| Silica, colloidal anhydrous, NF | 100 mg |
| Glycerin | 740 mg |
| Xylitol, NF | 800 mg |
| Sodium Citrate, USP | 100 mg |
| Saccharin Sodium cryst., USP, | 0.1 mg |
| Sodium Benzoate | 7.5 mg |
| Citric Acid Monohydrate, USP | 8.0 mg |
| Artificial Grape Flavor | 5 mg |
| FD&C Red # 40 Dye | 0.5 mg |
| Water | q.s |

Procedure for 1000 kg Batch:

Sodium polystyrene sulphonate USP (e.g. Amberlite® IRP 69 or Amberlite® 188N) is added to a carbetapentane citrate solution. Stir the mix for 12 hrs to allow complete drug/resin complex formation. The resultant insoluble drug/resin complex is separated and dried. The dried drug/resin complex is granulated with a delayed release/enteric polymer (e.g. Eudragit® L 100, Kollidon® MAE, Aquacoat® CPD) and the resultant granules are dried. If needed, the granules may be milled. In a suitably sized stainless steel vessel saccharin sodium, sodium benzoate, citric acid, and sodium citrate are dissolved in approximately 50 L of warm (about 45° C.) purified water. In another large stainless steel drum the silica, carbetapentane citrate ion-exchange complex, pseudoephedrine tannate and the chlorpheniramine tannate are mixed until a uniform and consistent mixture is obtained. In a separate 1000 L stainless steel tank which is equipped with a suitably sized homogenizer/disperser about 100 L of purified water is added. With the homogenizer on, the silica mixture containing carbetapentane citrate ion-exchange complex, pseudoephedrine tannate and the chlorpheniramine tannate is added to the stainless steel tank. Next, a previously prepared solution of saccharin sodium, sodium benzoate, citric acid, and sodium citrate are added to the tank. The first vessel is rinsed with about 2 L of water and the rinsate is transferred to the 1000 L tank. Finally, the remaining ingredients are added and homogenized for 15 minutes.

B. Extended Release Suspension Containing Phenylephrine for Night Time Administration An extended release suspension which contains a hydrocodone bitartrate ion-exchange complex, a dexchlorpheniramine maleate ion-exchange complex and a phenylephrine hydrochloride ion-exchange complex is illustrated as follows:

| Ingredients | Amount/5 ml |
|---|---|
| Hydrocodone Bitartrate Ion-Exchange Complex | Equivalent to 8 mg of Hydrocodone Bitartrate |
| Dexchlorpheniramine Maleate Ion-Exchange Complex | Equivalent to 6 mg of Dexchlorpheniramine Maleate |
| Phenylephrine HCl Ion-Exchange Complex | Equivalent to 10 mg of Phenylephrine HCl |
| Eudragit ® L 100 | 0.2 to 2.8 g |
| Glycerin | 315 mg |
| Polysorbate 80 | 1.5 mg |
| Carbomer (e.g., Carbopol ® 974) | 15 mg |
| Methyl Paraben | 9 mg |
| Propyl Paraben | 1 mg |
| Artificial Grape Flavor | 5 mg |
| FD&C Red # 40 Dye | 0.5 mg |
| Water | q.s |

The formula described above serves as a non-limiting example. Any active drug which is in the form of a salt, such as an antihistamine, codeine, or dihydrocodeine, can be incorporated as an ion-exchange resin complex.

Procedure:

Sodium polystyrene sulphonate USP (e.g. Amberlite® IRP 69) is added to a solution of dexchlorpheniramine maleate, hydrocodone bitartrate and phenylephrine HCl and the mixture is stirred for 12 hrs to allow complete drug/resin complex formation. The resultant insoluble drug/resin complex is separated and dried. The dried drug/resin complex is granulated with a delayed release/enteric polymer (e.g. Eudragit® L 100, Kollidon® MAE, Aquacoat® CPD) and the granules are dried. If needed, the granules may be milled. Next, in an appropriate amount of water the following ingredients are dissolved: Carbomer (e.g., Carbopol® 974), glycerin, polysorbate 80, methyl paraben, propyl paraben, artificial grape flavor, FD&C red #40 dye. To this suspension the milled granules are added as well as more water to make up to a final volume. To avoid settling of the suspension and to maintain a homogeneous product mixture agitation at a suitable rate has to be maintained. The product is filled in suitable containers.

Example 4

A. Bi-Layered Tablet Comprising Pseudoephedrine for Day Time Administration

A bi-layered tablet which comprises carbetapentane citrate in an immediate release layer and carbetapentane citrate, pseudoephedrine hydrochloride and chlorpheniramine maleate in a sustained release layer is illustrated as follows:

| Ingredients | Weight/tablet (mg) | Weight/1 kg batch (g) |
|---|---|---|
| Layer 1 (Immediate release) | | |
| Carbetapentane Citrate | 10.0 | 13.8 |
| Silicified Microcrystalline Cellulose | 111.0 | 153.1 |
| Povidone | 3.0 | 4.1 |
| Croscarmellose Sodium | 10.0 | 13.8 |
| Magnesium Stearate | 1.0 | 1.4 |
| Layer 2 (Sustained release) | | |
| Carbetapentane Citrate | 40 | 55.2 |
| Pseudoephedrine HCl | 60.0 | 82.8 |
| Chlorpheniramine Maleate | 8.0 | 11 |
| Microcrystalline Cellulose (PH 102) | 30.0 | 41.4 |
| Lactose Monohydrate | 100.0 | 137.9 |

-continued

| Ingredients | Weight/tablet (mg) | Weight/1 kg batch (g) |
| --- | --- | --- |
| Dicalcium Citrate | 100.0 | 137.9 |
| Povidone | 15.0 | 20.7 |
| Methocel K4M Premium | 212.0 | 292.4 |
| Stearic Acid | 20.0 | 27.6 |
| Magnesium Stearate | 5.0 | 6.9 |
| Total | 725.0 | 1000.0 |

Procedure:

(a) Immediate release layer #1: All ingredients are screened through a USP sieve size #30. Next, carbetapentane citrate, silicified microcrystalline cellulose and croscarmellose sodium are blended in a high shear mixer/granulator for 10 minutes and are granulated using a 30% povidone solution (4.1 g povidone in 13.7 g of solution). The granulation is dried until the LOD is less than 2.0%, followed by the step of screening the granules through a USP sieve size #14. The granules and the prescreened magnesium stearate (1.4 g) are added to the resultant blend and are mixed for 3 minutes.

(b) Sustained release layer #2: All ingredients are screened through a USP sieve size #30. Next, pseudoephedrine hydrochloride (87.5 g), chlorpheniramine maleate, carbetapentane citrate, microcrystalline cellulose PH 102, lactose monohydrate, dicalcium citrate, Methocel K4M Premium and stearic acid are blended in a high shear mixer/granulator for 10 minutes. The obtained blend is granulated using a 30% povidone solution (20.7 g povidone in 69 g of solution) and dried until the LOD is less than 2.0%. The granules are screened through a USP sieve size #14 and then added together with the prescreened magnesium stearate (6.9 g) to the above blend and mixed for 3 minutes.

Bi-layered tablets are manufactured using a rotary bi-layer tablet press, wherein the weight of the immediate release tablet layer is about 135 mg and the weight of the sustained release tablet layer is about 590 mg.

B. Bi-Layered Tablet Comprising Phenylephrine for Night Time Administration

A bi-layered tablet which comprises phenylephrine hydrochloride and carbinoxamine maleate in a first sustained release layer and codeine phosphate in a second sustained release layer is illustrated as follows:

| Ingredients | Weight/tablet (mg) | Weight/1 kg batch (g) |
| --- | --- | --- |
| Layer 1 (Sustained release) | | |
| Phenylephrine HCl | 75.0 | 185.2 |
| Carbinoxamine Maleate | 8.0 | 19.8 |
| Methocel K4M | 59.0 | 145.7 |
| Silicified Microcrystalline Cellulose | 30.0 | 74.1 |
| Eudragit NE | 15.0 | 37.0 |
| Magnesium Stearate | 3.0 | 7.4 |
| Layer 2 (Sustained release) | | |
| Codeine Phosphate | 30.0 | 74.1 |
| Microcrystalline Cellulose (PH 102) | 45.0 | 111.1 |
| Eudragit NE | 15.0 | 37.0 |
| Methocel K4M Premium | 100.0 | 246.9 |
| Stearic Acid | 20.0 | 49.4 |
| Magnesium Stearate | 5.0 | 12.3 |
| Total | 405.0 | 1000.0 |

Procedure:

(a) Sustained release layer #1: Phenylephrine HCl, carbinoxamine maleate, Methocel®K4M and silicified microcrystalline cellulose are mixed in a high shear mixer/granulator for 10 minutes. The resultant blend is granulated using a 30% povidone solution (3.0 g povidone in 10.0 g purified water). Upon completion of the granulation process, the wet mass is dried until the LOD is less than 2.0% and the granules are screened through a USP sieve size #14. The granules and prescreened magnesium stearate are added to a V shaped blender and are mixed for 3 minutes.

(b) Sustained release layer #2: All ingredients are screened through a USP sieve size #30. Codeine phosphate, Microcrustalline cellulose PH 102, and stearic acid are mixed in a high shear mixer/granulator for 10 minutes. The obtained blend is granulated using a 30% Eudragit® NE solution. Following, Methocel®K4M is added to the granulator and post mixed for 5 minutes. The granulation is dried until the LOD is less than 2.0% and the granules are screened through a USP sieve size #14. Finally, the granules and prescreened magnesium stearate are added to a V shaped blender and mixed for 3 minutes.

Bi-layered tablets are manufactured using a rotary bi-layer tablet press, wherein the weight of tablet layer #1 is about 190 mg and the weight of tablet layer #2 is about 215 mg. Capsules may be manufactured by filling the same proportions into capsules.

Example 5

A. Bi-Layered Tablet Comprising Pseudoephedrine for Day Time Administration

A bi-layered tablet which comprises pseudoephedrine hydrochloride and chlorpheniramine maleate in a first sustained release layer and codeine phosphate in a second sustained release layer is illustrated as follows:

| Ingredients | Weight/tablet (mg) | Weight/1 kg batch (g) |
| --- | --- | --- |
| Layer 1 (Sustained release) | | |
| Pseudoephedrine HCl | 120.0 | 253.2 |
| Chlorpheniramine Maleate | 12.0 | 25.3 |
| Methocel K4M | 70.0 | 147.7 |
| Silicified Microcrystalline Cellulose | 35.0 | 73.9 |
| Eudragit NE | 20.0 | 42.2 |
| Magnesium Stearate | 3.0 | 6.3 |
| Layer 2 (Sustained release) | | |
| Codeine Phosphate | 30.0 | 63.3 |
| Microcrystalline Cellulose (PH 102) | 45.0 | 95.0 |
| Eudragit NE | 15.0 | 31.7 |
| Methocel K4M Premium | 100.0 | 211.0 |
| Stearic Acid | 20.0 | 42.2 |
| Magnesium Stearate | 5.0 | 10.6 |
| Total | 475.0 | 1000.0 |

Procedure:

(a) Sustained release layer #1: Pseudoephedrine HCl, chlorpheniramine maleate, Methocel®K4M and silicified microcrystalline cellulose are mixed in a high shear mixer/granulator for 10 minutes. The obtained blend is granulated using Eudragit® NE (30%). The resultant granulation mixture is dried until the LOD is less than 2.0% and then screened through a USP sieve size #14. Finally, the granules and prescreened magnesium stearate are added in a V shaped blender and mixed for 3 minutes.

(b) Sustained release layer #2: All ingredients are screened through a USP sieve size #30. Codeine phosphate, microcrystalline cellulose PH 102, and stearic acid are mixed in a high shear mixer/granulator for 10 minutes. The obtained blend is granulated using a 30% Eudragit® NE solution. Next, Methocel®K4M is added to the granulator and post mixed for 5 minutes. The granulation is dried until the LOD is less than 2.0% and the granules are screened through a USP sieve size #14 Finally, the granules and prescreened magnesium stearate are added to a V shaped blender and mixed for 3 minutes.

Bi-layered tablets are manufactured using a rotary bi-layer tablet press, wherein the weight of tablet layer #1 is about 260 mg and the weight of tablet layer #2 is about 215 mg. Capsules may be manufactured by filling the same proportions into capsules.

B. Bi-Layered Tablet Comprising Phenylephrine for Night Time Administration

A bi-layered tablet which comprises guaifenesin in a first sustained release layer and codeine phosphate and phenylephrine hydrochloride in a second sustained release layer is illustrated as follows:

| Ingredients | Weight/tablet (mg) | Weight/1 kg batch (g) |
|---|---|---|
| Layer 1 (Sustained release) | | |
| Guaifenesin | 600.0 | 558.0 |
| Methocel K15M | 100.0 | 93.0 |
| Silicified Microcrystalline Cellulose | 50 | 46.5 |
| Eudragit NE | 42 | 39.1 |
| Magnesium Stearate | 8.0 | 7.4 |
| Layer 2 (Sustained release) | | |
| Codeine Phosphate | 30.0 | 27.9 |
| Phenylephrine HCl | 60.0 | 55.8 |
| Microcrystalline Cellulose (PH 102) | 45.0 | 41.9 |
| Eudragit NE | 15.0 | 14.0 |
| Methocel K4M Premium | 100.0 | 93.0 |
| Stearic Acid | 20.0 | 18.6 |
| Magnesium Stearate | 5.0 | 4.7 |
| Total | 1075.0 | 1000.0 |

Procedure:

(a) Sustained release layer #1: Guaifenesin, Methocel®K15M and silicified microcrystalline cellulose are mixed in a high shear mixer/granulator for 10 minutes. The obtained blend is granulated using Eudragit® NE (30%). Next, the granulation mixture is dried until the LOD is less than 2.0% and then screened through a USP sieve size #14. Finally, the granules and prescreened magnesium stearate are added in a V shaped blender and mixed for 3 minutes.

(b) Sustained release layer #2: All ingredients are screened through a USP sieve size #30. Codeine phosphate, phenylephrine HCl, microcrystalline cellulose PH 102, dicalcium phosphate and stearic acid are mixed in a high shear mixer/granulator for 10 minutes. The obtained blend is granulated using a 30% Eudragit® NE solution. Next, Methocel®K4M is added to the granulator and post mixed for 5 minutes. The granulation is dried until the LOD is less than 2.0% and the granules are screened through a USP sieve size #14 Finally, the granules and prescreened magnesium stearate are added to a V shaped blender and mixed for 3 minutes.

Bi-layered tablets are manufactured using a rotary bi-layer tablet press, wherein the weight of tablet layer #1 is about 800 mg and the weight of tablet layer #2 is about 275 mg. Capsules may be manufactured by filling the same proportions into capsules.

Example 6

A. Bi-Layered Tablet Comprising Pseudoephedrine for Day Time Administration A bi-layered tablet which comprises promethazine hydrochloride in an immediate release layer and codeine phosphate and pseudoephedrine hydrochloride in a sustained release layer is illustrated as follows:

| Ingredients | Weight/tablet (mg) | Weight/1 kg batch (g) |
|---|---|---|
| Layer 1 (Immediate release) | | |
| Promethazine HCl | 25.0 | 37.0 |
| Silicified Microcrystalline Cellulose | 111.0 | 164.3 |
| Povidone | 3.0 | 4.4 |
| Croscarmellose Sodium | 10.0 | 14.8 |
| Magnesium Stearate | 1.0 | 1.5 |
| Layer 2 (Sustained release) | | |
| Codeine Phosphate | 30.0 | 44.4 |
| Pseudoephedrine HCl | 120.0 | 177.6 |
| Microcrystalline Cellulose (PH 102) | 30.0 | 44.4 |
| Dicalcium Phosphate | 100.0 | 148.0 |
| Povidone | 15.0 | 22.2 |
| Methocel K4M Premium | 205.0 | 303.4 |
| Stearic Acid | 20.0 | 29.6 |
| Magnesium Stearate | 5.0 | 7.4 |
| Total | 675.0 | 1000.0 |

Procedure:

(a) Immediate release layer #1: Promethazine HCl, silicified microcrystalline cellulose and croscarmellose sodium are mixed in a high shear mixer/granulator for 10 minutes. The resultant blend is granulated using a 30% povidone solution (3.0 g povidone in 10.0 g purified water). Upon completion of the granulation process, the wet mass is dried until the LOD is less than 2.0% and the granules are screened through a USP sieve size #14. The granules and prescreened magnesium stearate are added to a V shaped blender and are mixed for 3 minutes.

(b) Sustained release layer #2: Codeine phosphate, pseudoephedrine HCl, microcrystalline cellulose PH 102, dicalcium phosphate, Methocel K4M Premium and stearic acid are mixed in a high shear mixer/granulator for 10 minutes. The obtained blend is granulated using a 30% povidone solution (15.0 g povidone in 50.0 g purified water). The resultant granulation is dried until the LOD is less than 2.0% and the granules are screened through a USP sieve size #14. The granules and prescreened magnesium stearate are added in a V shaped blender and mixed for 3 minutes.

Bi-layered tablets are manufactured using a rotary bi-layer tablet press, wherein the weight of tablet layer #1 is about 150 mg and the weight of tablet layer #2 is about 525 mg. Capsules may be manufactured by filling the same proportions into capsules.

B: Bi-Layered Tablet Comprising Phenylephrine for Night Time Administration A bilayered tablet which comprises codeine phosphate in a first sustained release layer and phenylephrine hydrochloride and chlorpheniramine maleate in a second sustained release layer is illustrated as follows:

| Ingredients | Weight/tablet (mg) | Weight/1 kg batch (g) |
|---|---|---|
| Layer 1 (Sustained release) | | |
| Codeine Phosphate | 30 | 54.5 |
| Methocel K4M | 50 | 90.9 |
| Silicified Microcrystalline Cellulose | 100.0 | 181.8 |
| Sodium Starch Glycolate | 10.0 | 18.2 |
| Magnesium Stearate | 1.0 | 1.8 |
| Layer 2 (Sustained release) | | |
| Phenylephrine HCl | 60 | 109 |
| Chlorpheniramine Maleate | 8.0 | 14.5 |
| Lactose Monohydrate | 50.0 | 90.9 |
| Dicalcium Phosphate | 50.0 | 90.9 |
| Methocel K4M | 181.0 | 329.1 |
| Stearic acid | 15.0 | 27.3 |
| Magnesium Stearate | 5.0 | 9.1 |
| Total | 550.0 | 1000.0 |

Procedure:

(a) Sustained release Layer #1: All ingredients are screened through a USP sieve size #30. Further, a portion of the Kollidon SR (145 g) and all the codeine phosphate are pre-blended for 15 minutes. Lactose monohydrate (90.9 gms) and dicalcium phosphate (90.9 g) are added to the above pre-blend and mixed for an additional 20 minutes. Thereafter stearic acid (27.3 g) and magnesium stearate (9.1 g) are added to the above blend and mixed for three minutes.

(b) Sustained release layer #2: All ingredients are screened through a USP sieve size #30. Further, a portion of the Kollidon SR (145 g) and all the chlorpheniramine maleate (14.5 g) are pre-blended for 15 minutes. The remaining Kollidon SR (313.2 g), phenylephrine hydrochloride (36.4 g), lactose monohydrate (90.9 g) and dicalcium phosphate (90.9 g) are added to the above pre-blend and mixed for additional 20 minutes. Stearic acid (27.3 g) and magnesium stearate (9.1 gms) are added to the above blend and mixed for three minutes.

Bi-layered tablets are manufactured using a rotary bi-layer tablet press, wherein the weight of tablet layer #1 is about 150 mg and the weight of tablet layer #2 is about 400 mg. Capsules may be manufactured by filling the same proportions into capsules.

Example 7

A. Bi-Layered Tablet Comprising Pseudoephedrine for Day Time Administration

A bi-layered tablet which comprises codeine phosphate in an immediate release layer and codeine phosphate, pseudoephedrine hydrochloride and chlorpheniramine maleate in a sustained release layer for day time administration is illustrated as follows:

| Ingredients | Weight/tablet (mg) | Weight/1 kg batch (g) |
|---|---|---|
| Layer 1 (Immediate release) | | |
| Codeine Phosphate | 10.0 | 11.9 |
| Silicified Microcrystalline Cellulose | 111.0 | 158.6 |
| Povidone | 3.0 | 4.3 |
| Croscarmellose Sodium | 10.0 | 14.3 |
| Magnesium Stearate | 1.0 | 1.4 |
| Layer 2 (Sustained release) | | |
| Codeine Phosphate | 30.0 | 35.7 |
| Pseudoephedrine HCl | 60.0 | 85.7 |
| Chlorpheniramine Maleate | 8.0 | 11.4 |
| Microcrystalline Cellulose (PH 102) | 30.0 | 42.9 |
| Lactose Monohydrate | 100.0 | 142.9 |
| Dicalcium Phosphate | 100.0 | 142.9 |
| Povidone | 15.0 | 21.4 |
| Methocel K4M Premium | 212.0 | 302.9 |
| Stearic Acid | 20.0 | 28.6 |
| Magnesium Stearate | 5.0 | 7.1 |
| Total | 700.0 | 1012.0 |

Procedure:

(a) Immediate release layer #1: All ingredients are screened through a USP sieve size #30. Codeine phosphate (11.9 g), silicified microcrystalline cellulose (158.6 g), and croscarmellose sodium are blended in a high shear mixer/granulator for 10 minutes. The resultant blend is granulated using a 30% povidone solution (4.3 g povidone in 14.3 g purified water). The resultant granulation is dried until the LOD is less than 2.0% and the granules are screened through a USP sieve size #14. The granules and the prescreened magnesium stearate (1.4 gms) are added to the above blend and mixed for 3 minutes.

(b) Sustained release layer #2: All ingredients are screened through a USP sieve size #30. Pseudoephedrine hydrochloride, chlorpheniramine maleate, codeine phosphate, microcrystalline cellulose PH 102, lactose monohydrate, dicalcium phosphate, Methocel K4M Premium and stearic acid are blended in a high shear mixer/granulator for 10 minutes. The resultant blend is granulated using a 30% povidone solution (21.4 g povidone in 71.3 g purified water). The resultant granulation is dried until the LOD is less than 2.0% and the granules are screened through a USP sieve size #14 Finally, the granules and the prescreened magnesium stearate are added to the above blend and mixed for 3 minutes.

Bi-layered tablets are manufactured using a rotary bi-layer tablet press, wherein the weight of tablet layer #1 is about 150 mg and the weight of tablet layer #2 is about 550 mg.

B. Bi-Layered Tablet Containing Phenylephrine for Night Time Administration

A bi-layered tablet which comprises guaifenesin in a first sustained release layer and codeine phosphate and phenylephrine hydrochloride in a second sustained release layer is illustrated as follows:

| Ingredients | Weight/tablet (mg) | Weight/1 kg batch (g) |
|---|---|---|
| Layer 1 (Sustained release) | | |
| Guaifenesin | 1000.0 | 635.0 |
| Methocel K15M | 200.0 | 127.0 |
| Silicified Microcrystalline Cellulose | 40.0 | 25.4 |
| Eudragit NE | 50.0 | 31.8 |
| Magnesium Stearate | 10.0 | 6.4 |
| Layer 2 (Sustained release) | | |
| Codeine Phosphate | 30.0 | 19.1 |
| Phenylephrine HCl | 60.0 | 38.1 |
| Microcrystalline Cellulose (PH 102) | 45.0 | 28.6 |

-continued

| Ingredients | Weight/tablet (mg) | Weight/1 kg batch (g) |
|---|---|---|
| Eudragit NE | 15.0 | 9.5 |
| Methocel K4M Premium | 100.0 | 63.5 |
| Stearic Acid | 20.0 | 12.7 |
| Magnesium Stearate | 5.0 | 3.2 |
| Total | 1575.0 | 1000.0 |

Procedure:

(a) Sustained release layer #1: Guaifenesin, Methocel®K15M and silicified microcrystalline cellulose are mixed in a high shear mixer/granulator for 10 minutes. The resultant blend is granulated using a Eudragit® NE (30%). Next, the granulation is dried until the LOD is less than 2.0% and the granules are screened through a USP sieve size #14 Finally, the granules and the prescreened magnesium stearate are added in a V shaped blender and mixed for 3 minutes.

(b) Sustained release layer #2: All ingredients are screened through a USP sieve size #30. Codeine phosphate, phenylephrine HCl, microcrystalline cellulose PH 102, dicalcium phosphate and stearic acid are mixed in a high shear mixer/granulator for 10 minutes. The above blend is granulated using a Eudragit® NE (30%), followed by the addition of Methocel®K4M to the granulator and post mixing for 5 minutes. The granulation is dried until the LOD is less than 2.0% and the granules are screened through a USP sieve size #14. Finally, the granules and the prescreened magnesium stearate are added to a V shaped blender and are mixed for 3 minutes.

Bi-layered tablets are manufactured using a rotary bi-layer tablet press, wherein the weight of tablet layer #1 is about 1300 mg and the weight of tablet layer #2 is 275 mg. Capsules may be manufactured by filling the same proportions into capsules.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A regimen for the alleviation of a condition which comprises nasal congestion, wherein the regimen comprises administering to a subject in need thereof one or more first dosage units which comprise at least one of pseudoephedrine and a pharmaceutically acceptable salt thereof in an amount which is sufficient to maintain a therapeutically effective plasma level of pseudoephedrine for a first period, and subsequently administering to the subject one or more second dosage units which are different from the first dosage units and comprise at least one of phenylephrine and a pharmaceutically acceptable salt thereof in an amount which is sufficient to maintain a therapeutically effective plasma level of phenylephrine for a second period, the first and second dosage units being administered such that there is substantially no gap between the first and second periods.

2. The regimen of claim 1, wherein there is substantially no overlap between the first and second periods.

3. The regimen of claim 1, wherein the first period and the second period together are about 24 hours long.

4. The regimen of claim 1, wherein the first period is from about 12 hours to about 16 hours long.

5. The regimen of claim 1, wherein a one-time administration of the one or more first dosage units is sufficient to maintain a therapeutically effective plasma level of pseudoephedrine over the entire first period.

6. The regimen of claim 5, wherein a one-time administration of the one or more second dosage units is sufficient to maintain a therapeutically effective plasma level of phenylephrine over the entire second period.

7. The regimen of claim 1, wherein the first period substantially coincides with a period during which the subject intends to be awake and the second period substantially coincides with a period during which the subject intends to be asleep.

8. The regimen of claim 1, wherein the administration of the one or more first dosage units and the subsequent administration of the one or more second dosage units is repeated at least once.

9. The regimen of claim 1, wherein a minimum therapeutically effective plasma level of pseudoephedrine is not substantially exceeded over the entire first period.

10. The regimen of claim 1, wherein at least one of the first and second dosage units further comprises at least one additional active ingredient.

11. The regimen of claim 10, wherein the at least one additional active ingredient comprises one or more of an antihistamine, a cough suppressant, an expectorant, an analgesic and an anti-inflammatory agent.

12. The regimen of claim 10, wherein the first and second dosage units each independently further comprise at least one additional active ingredient which comprises one or more of an antihistamine, a cough suppressant, an expectorant, an analgesic and an anti-inflammatory agent.

13. The regimen of claim 10, wherein a period of a therapeutic plasma level of the at least one additional active ingredient overlaps with at least about 70% of the first period or of the second period.

14. The regimen of claim 1, wherein the one or more first dosage units are free of phenylephrine and a pharmaceutically acceptable salt thereof and the one or more second dosage units are free of pseudoephedrine and a pharmaceutically acceptable salt thereof.

15. A regimen for the alleviation of a condition which comprises nasal congestion, wherein the regimen comprises administering to a subject in need thereof one or more first dosage units which comprise at least one of pseudoephedrine and a pharmaceutically acceptable salt thereof and at least one additional active ingredient selected from antihistamines, cough suppressants, expectorants, analgesics and anti-inflammatory agents, the amount of the one or more first dosage units being sufficient to maintain a therapeutically effective plasma level of pseudoephedrine for a first period, and subsequently administering to the subject one or more second dosage units which comprise at least one of phenylephrine and a pharmaceutically acceptable salt thereof and at least one additional active ingredient selected from antihistamines, cough suppressants, expectorants, analgesics and anti-inflammatory agents, the amount of the one or more second dosage units being sufficient to maintain a therapeutically effective plasma level of phenylephrine for a second period, wherein the first and second dosage units are administered such that there is substantially no overlap and substantially no gap between the first and second periods and wherein the administration of the one or more first dosage units and the subsequent administration of the one or more second dosage units is repeated at least once.

16. The regimen of claim 15, wherein the one or more first dosage units are free of phenylephrine and a pharmaceutically acceptable salt thereof and the one or more second dosage units are free of pseudoephedrine and a pharmaceutically acceptable salt thereof.

17. The regimen of claim 15, wherein the first period substantially coincides with a period during which the subject intends to be awake and the second period substantially coincides with a period during which the subject intends to be asleep.

18. The regimen of claim 15, wherein a minimum therapeutically effective plasma level of pseudoephedrine is not substantially exceeded over the entire first period.

19. The regimen of claim 1, wherein the first and second dosage units are different from each other and at least one of the first and second dosage units at least one of (i) comprises an antihistamine, (ii) is free of an expectorant and (iii) is free of a cough suppressant.

20. The regimen of claim 19, wherein the first dosage units may further comprise one or more additional active ingredients which are selected from chlorpheniramine, promethazine, carbetapentane, codeine and pharmaceutically acceptable salts thereof and/or the second dosage units may further comprise one or more additional active ingredients which are selected from chlorpheniramine, dexchlorpheniramine, carbinoxamine, hydrocodone, codeine, guaifenesin and pharmaceutically acceptable salts thereof.

* * * * *